United States Patent [19]

Lun et al.

[11] Patent Number: 5,342,325
[45] Date of Patent: Aug. 30, 1994

[54] INTRODUCER NEEDLE AND CATHETER ASSEMBLY

[75] Inventors: Warren D. Lun, Battle Creek; Paul F. Rom, Kentwood; William M. Booth, Paw Paw, all of Mich.

[73] Assignee: DLP, Incorporated, Grand Rapids, Mich.

[21] Appl. No.: 986,527

[22] Filed: Dec. 7, 1992

[51] Int. Cl.⁵ .................................. A61M 27/00
[52] U.S. Cl. .............................. 604/272; 604/280
[58] Field of Search ............... 604/158, 160, 161, 164, 604/177, 264, 272, 280

[56] References Cited

U.S. PATENT DOCUMENTS

| | | |
|---|---|---|
| 3,537,451 | 11/1970 | Beck et al. |
| 3,861,393 | 1/1975 | Durand |
| 3,877,429 | 4/1975 | Rasumoff |
| 3,920,013 | 11/1975 | Bodzin ........................ 604/158 |
| 4,449,973 | 5/1984 | Luther |
| 4,490,136 | 12/1984 | Ekbladh et al. |
| 4,496,353 | 1/1985 | Overland et al. |
| 4,518,383 | 5/1985 | Evans ........................... 604/51 |
| 4,617,019 | 10/1986 | Fecht et al. |
| 4,684,369 | 8/1987 | Wildemeersch |
| 4,792,328 | 12/1988 | Beck et al. |
| 4,805,292 | 2/1989 | Noguchi |
| 4,869,259 | 9/1989 | Elkins ........................... 128/660 |
| 4,883,474 | 11/1989 | Sheridan et al. |
| 4,936,834 | 6/1990 | Beck et al. |
| 4,976,684 | 12/1990 | Broadnax, Jr. |
| 5,085,631 | 2/1992 | Leighton ....................... 604/28 |
| 5,100,390 | 3/1992 | Lubeck et al. ................. 604/158 |

OTHER PUBLICATIONS

British Medical Journal, Feb. 23, 1952 p. 435 "An Introducer for Plastic Cannuloe", Dr. Mitchell.

*Primary Examiner*—C. Fred Rosenbaum
*Assistant Examiner*—Corrine Maglione
*Attorney, Agent, or Firm*—Varnum, Riddering, Schmidt & Howlett

[57] ABSTRACT

A catheter assembly for the sterile introduction of a catheter into a body cavity is disclosed. The catheter assembly comprises a catheter, a stylet received within the catheter and a needle selectively mounted on one end of the catheter. Gripping means are incorporated on one or more of the stylet, needle or catheter to selectively mount the needle to the catheter.

29 Claims, 6 Drawing Sheets

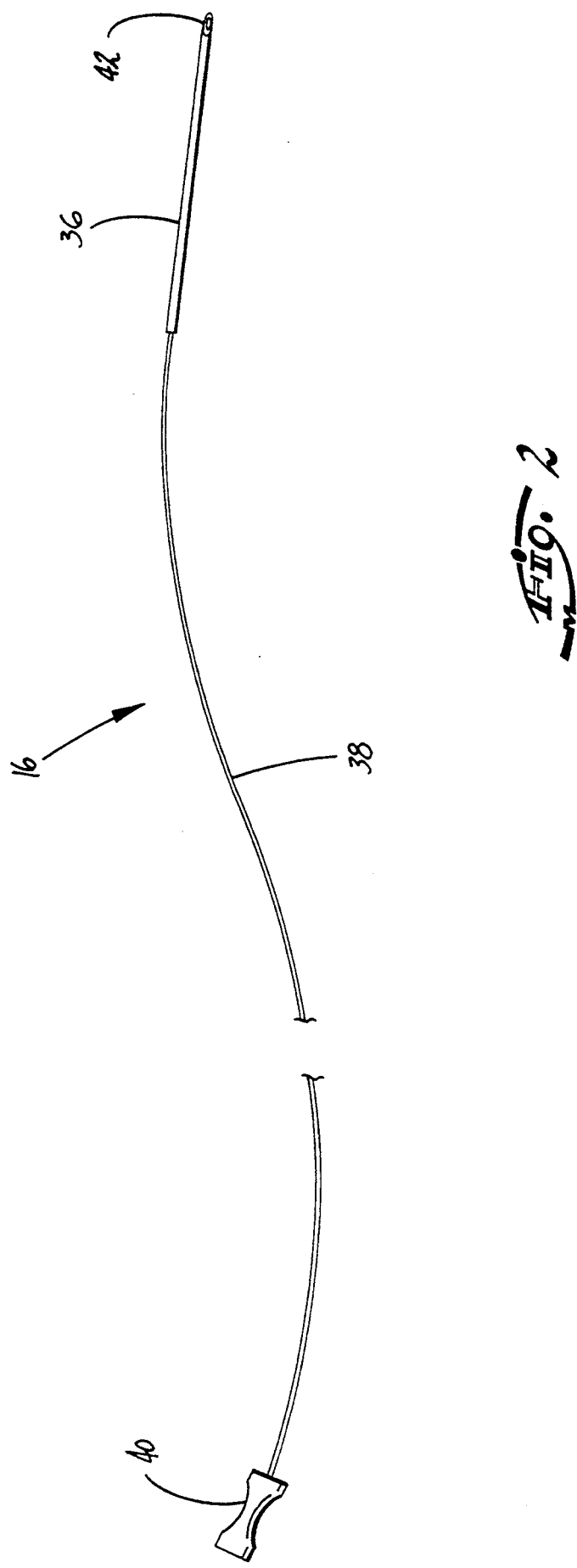

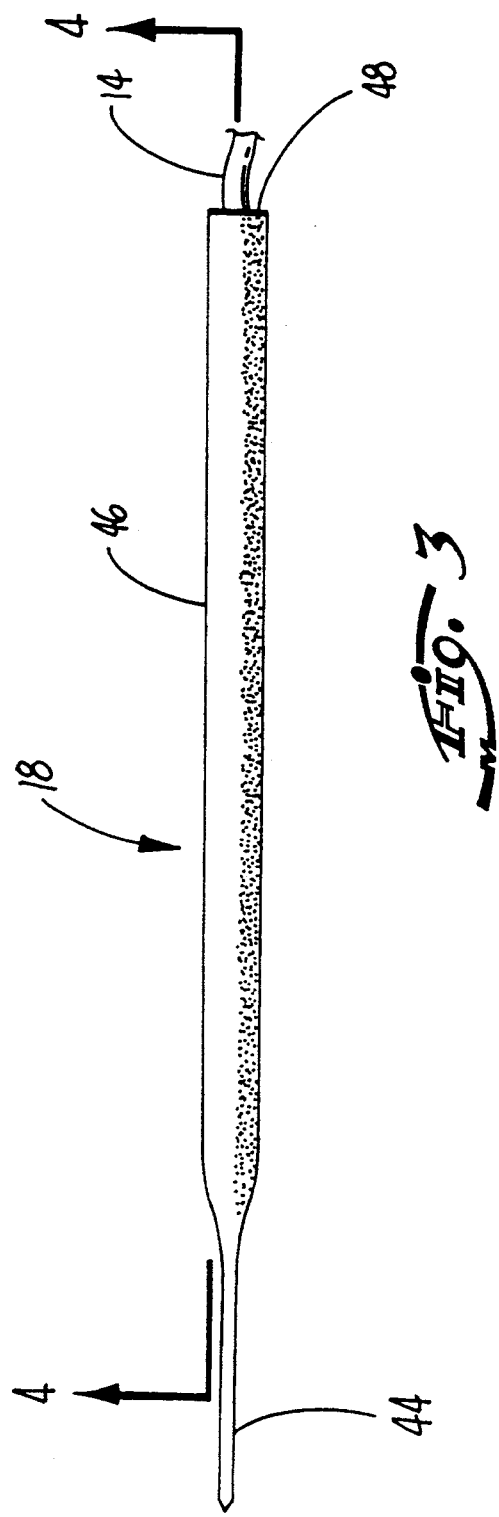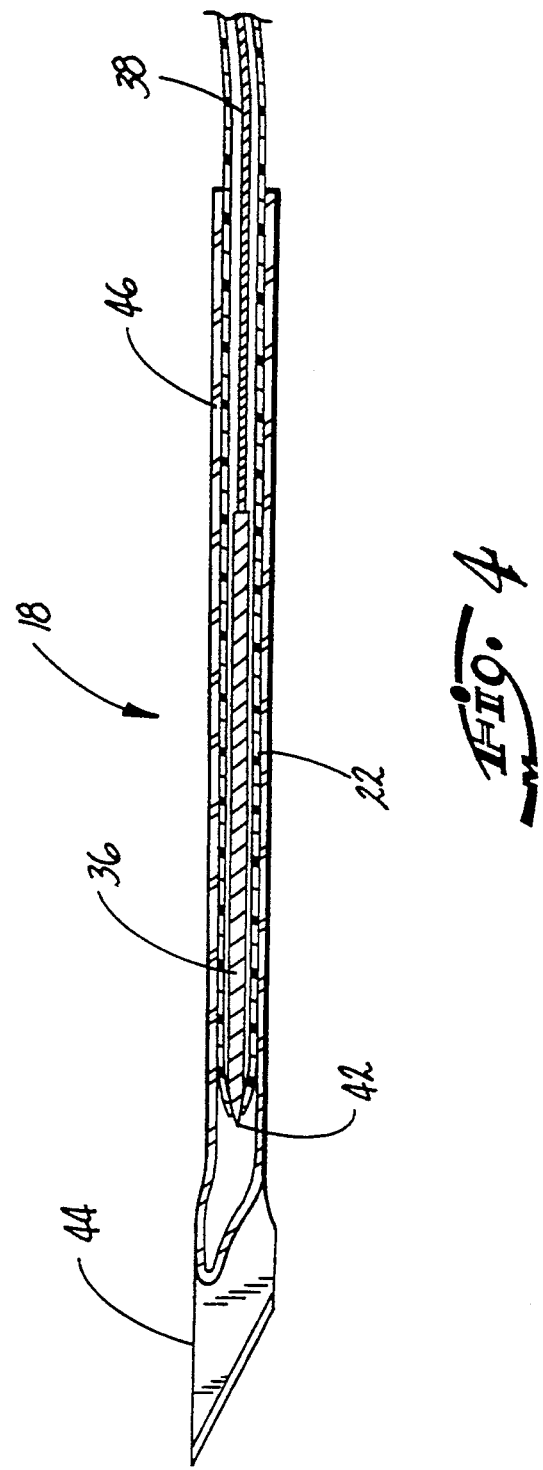

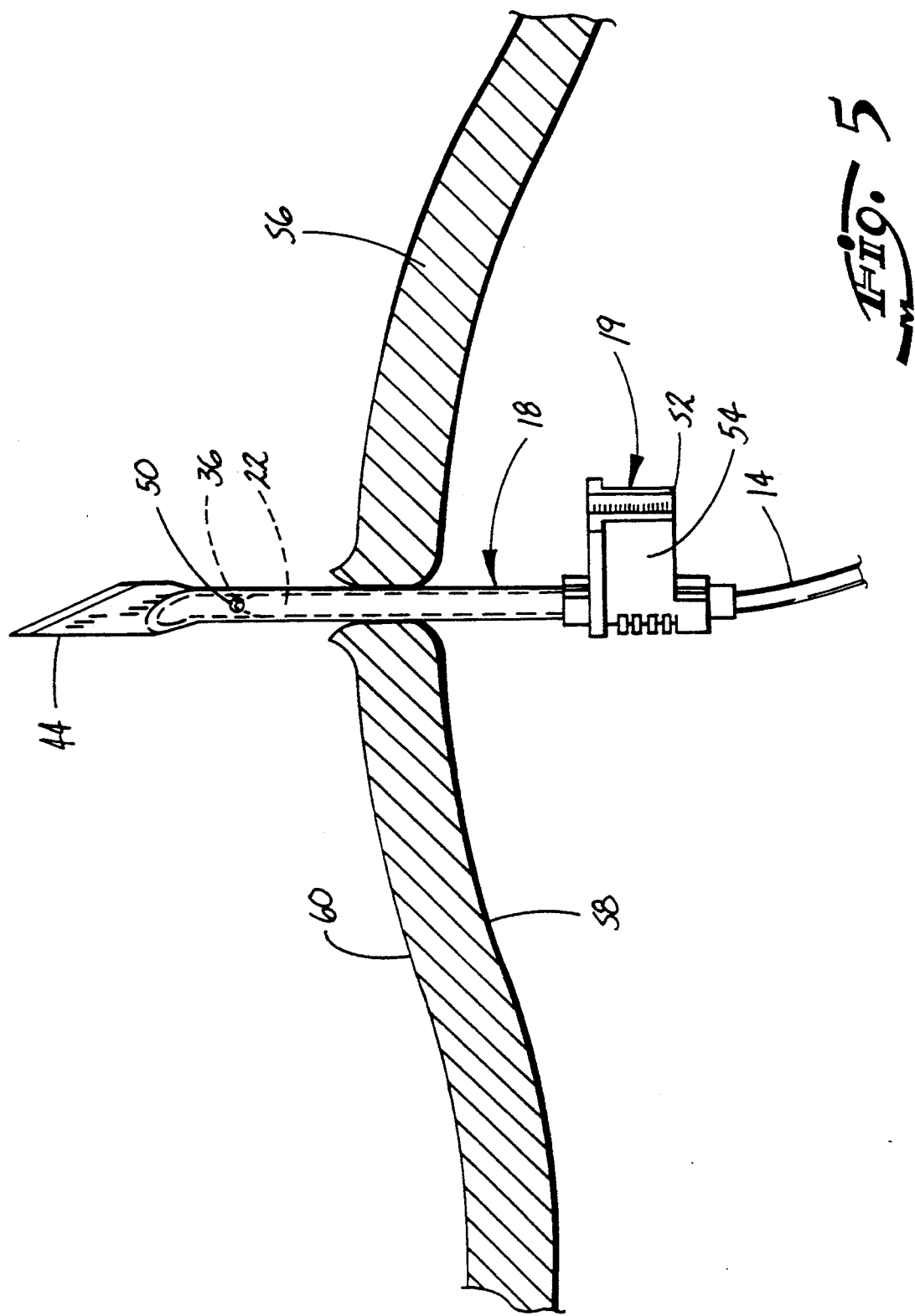

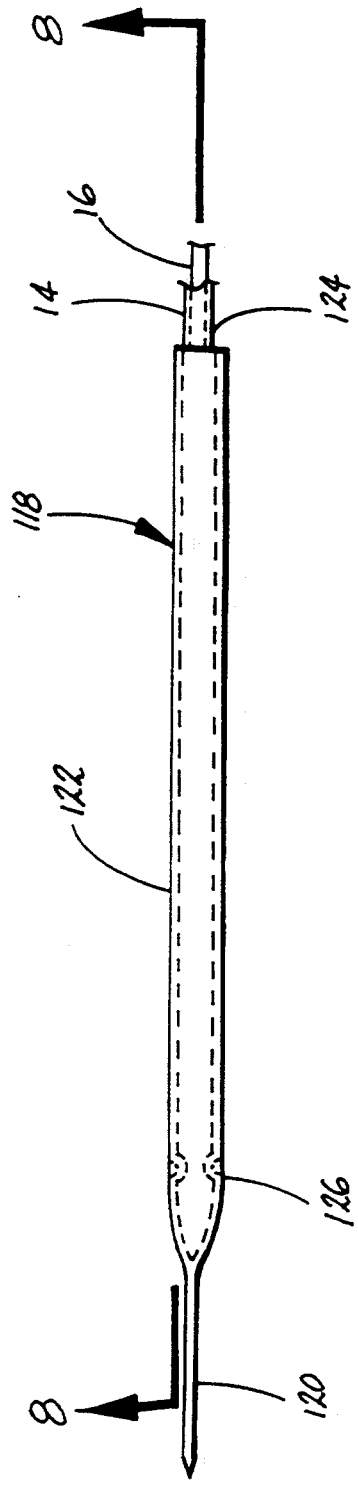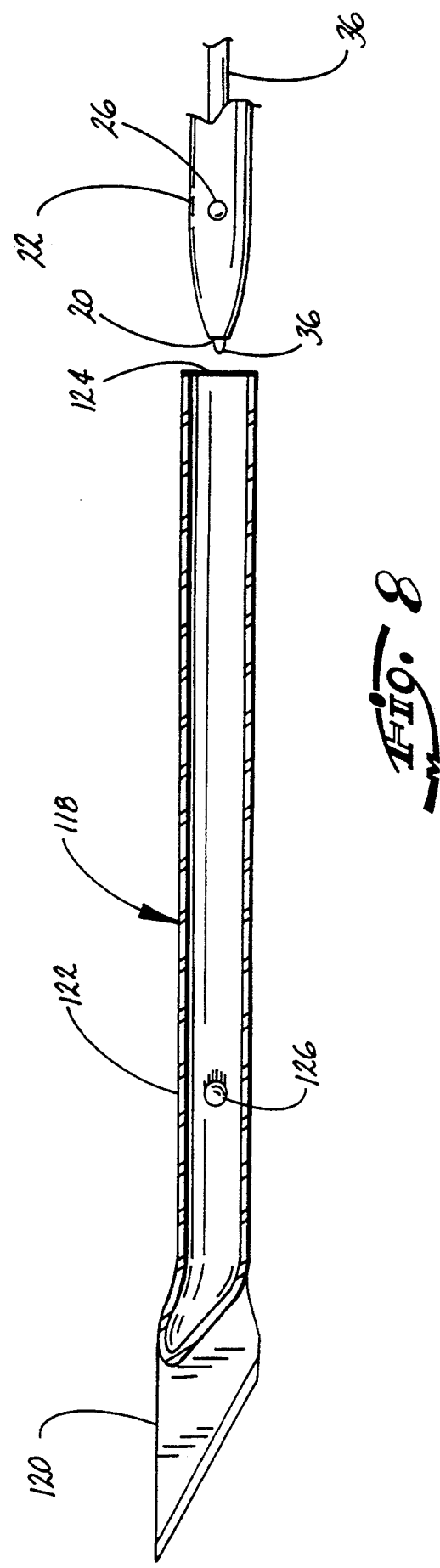

INTRODUCER NEEDLE AND CATHETER ASSEMBLY

BACKGROUND OF THE INVENTION

1. Field of the Invention

This invention relates to a catheter assembly for sensing internal fluid pressure and aspirating fluids from a wound and, more particularly, to a needle for inserting the catheter assembly in the body tissue.

2. Description of Related Art

Following surgical procedures in or around the human heart, it is often desirable to monitor the pressure of the fluid in or around the heart. More particularly, it is desirable to measure the pressure of the blood within the left atrium of the heart. The pressure is measured by inserting one end of a fluid-filled catheter into the superior pulmonary vein and attaching the other end of the fluid-filled catheter to a pressure sensing device. This is commonly known as a left atrial catheter. Monitoring the left atrium pressure with a left atrial catheter is one way of measuring the strength of the heart following surgery and in evaluating the proper time to remove a heart pump from a heart surgery patient. The sterility of the end of the catheter which is mounted in the superior pulmonary vein is paramount. The introduction of infection causing microorganisms into the heart can be deadly.

The left atrial catheter is typically mounted in the body cavity through an incision in the skin and body tissue or through an opening created by a catheter needle. The catheter assembly can be inserted "inside to outside", i.e. from the wound side to the external skin surface, or it can be inserted "outside to inside", i.e. from the skin surface through the body tissue to the wound side. Regardless of the method of introducing the catheter, it is imperative that all steps be taken to reduce to a minimum the chance of infection of the wound.

Examples of catheter needles which are mounted inside to outside are disclosed in U.S. Pat. No. 4,976,684 to Broadnax, Jr. and U.S. Pat. No. 4,792,328 to Beck et al. Each of these catheter assemblies includes a needle or trocar which is first used to create an opening in the skin and body tissue and then to guide the catheter from the wound side of the body tissue to the external skin surface.

The more traditional procedure for inserting the catheter is outside to inside. However, this procedure has one significant drawback. Even when the skin has been assiduously prepared, introducing the needle from the external skin surface can result in the introduction of microorganisms from the skin into the wound via the needle. Unfortunately, known catheter assemblies are not adapted to prevent or reduce exposure of the catheter to the potentially contaminated external skin surface. Examples of known catheter assemblies which do not address this problem are disclosed in U.S. Pat. No. 3,861,393 to Durand, U.S. Pat. No. 4,496,353 to Overland et al., U.S. Pat. No. 4,490,136 to Ekbladh et al., U.S. Pat. No. 4,617,019 to Fecht et al. and U.S. Pat. No. 4,883,474 to Sheridan et al.

Another known method of introducing the catheter is to use a catheter having an internal stylet. The catheter and internal stylet are passed through the skin and body tissue outside to inside. Unfortunately, this procedure can result in damage to the catheter when passing through the skin. For example, the tip of the catheter can slide back on the internal stylet similar to an accordion, thereby damaging the fragile catheter tip. Secondly, microorganisms present on the skin surface can become lodged inside the catheter tip and the bevel of the stylet. This procedure is not acceptable.

Catheters are also mounted in a body cavity to remove fluids within the body cavity. Body tissue that has been subject to a wound or an internal surgical procedure often secretes fluid. It is necessary to remove fluid thus secreted within a body cavity in order to promote healing and prevent infection of the wound. Catheters have long been used to aspirate secreted fluid from a wound in a body cavity. These catheters are often mounted inside to outside and outside to inside as discussed above.

SUMMARY OF INVENTION

The catheter assembly according to the invention provides a removable needle mounted to one end of a catheter which effectively shields the portion of the catheter introduced into the body cavity from microorganisms carried on the external skin surface of the patient. The catheter assembly according to the invention also provides efficient means for inserting the catheter through the skin of the patient.

The invention comprises a catheter assembly and needle used therein for mounting a catheter in a body cavity. The catheter has a proximal end, a distal end opposite the proximal end, and a lumen extending therethrough. The needle comprises an elongate body having a hollow portion, a proximal end, and a distal end opposite to the proximal end. The distal end of the needle closes the hollow portion and comprises a sharpened tip. The proximal end of the body is open and in communication with the hollow portion for receiving the distal end of the catheter in the hollow portion. A stylet is telescopically received within the lumen of the catheter. The stylet has a distal and a proximal end, the proximal end being opposite the distal end. The distal end of the stylet comprises a rigid introducer needle having a slight longitudinal bend imparted to the introducer needle such that the catheter is frictionally retained within the hollow portion of the needle.

In another aspect, the invention comprises a catheter assembly having a catheter with a proximal end, a distal end and a lumen extending therethrough and a needle having an elongate body, at least a portion of which is hollow. The needle further has a distal end and a proximal end, the distal end comprising a sharpened tip. The proximal end of the hollow needle is open and is in communication with the hollow portion for receiving the distal end of the catheter. The invention further comprises at least one detent protruding inwardly from the interior surface of the hollow portion to limit the length of the distal end of the catheter received in the hollow portion of the needle and to releasably hold the catheter within the hollow portion of the needle.

Preferably, a pair of diametrically opposed detents protruding inwardly from the interior surface of the hollow portion are incorporated on the needle. The detents limit the received length of the distal end of the catheter.

In another embodiment, the means for releasably holding the catheter comprises a slight longitudinal bend or radius imparted to either the introducer needle of the stylet or the hollow body of the needle. The slight bend serves to frictionally engage the stylet and catheter within the hollow portion of the needle.

BRIEF DESCRIPTION OF THE DRAWINGS

The invention will now be described with reference to the drawings wherein:

FIG. 2 is an elevational view of a styler for use with a catheter assembly according to the invention;

FIG. 3 is a top view of a first embodiment of the catheter needle for use with the catheter assembly according to the invention;

FIG. 4 is a partial sectional side view of the catheter needle of FIG. 3;

FIG. 5 is a side view of the catheter assembly according to the invention partially inserted through body tissue;

FIG. 7 is a top view of a second embodiment of the catheter needle for use with a catheter assembly according to the invention; and FIG. 8 is a partial sectional side view of the second embodiment of the catheter needle as seen in FIG. 7 with the catheter and stylet removed therefrom.

DESCRIPTION OF THE PREFERRED EMBODIMENTS

Figure 1:
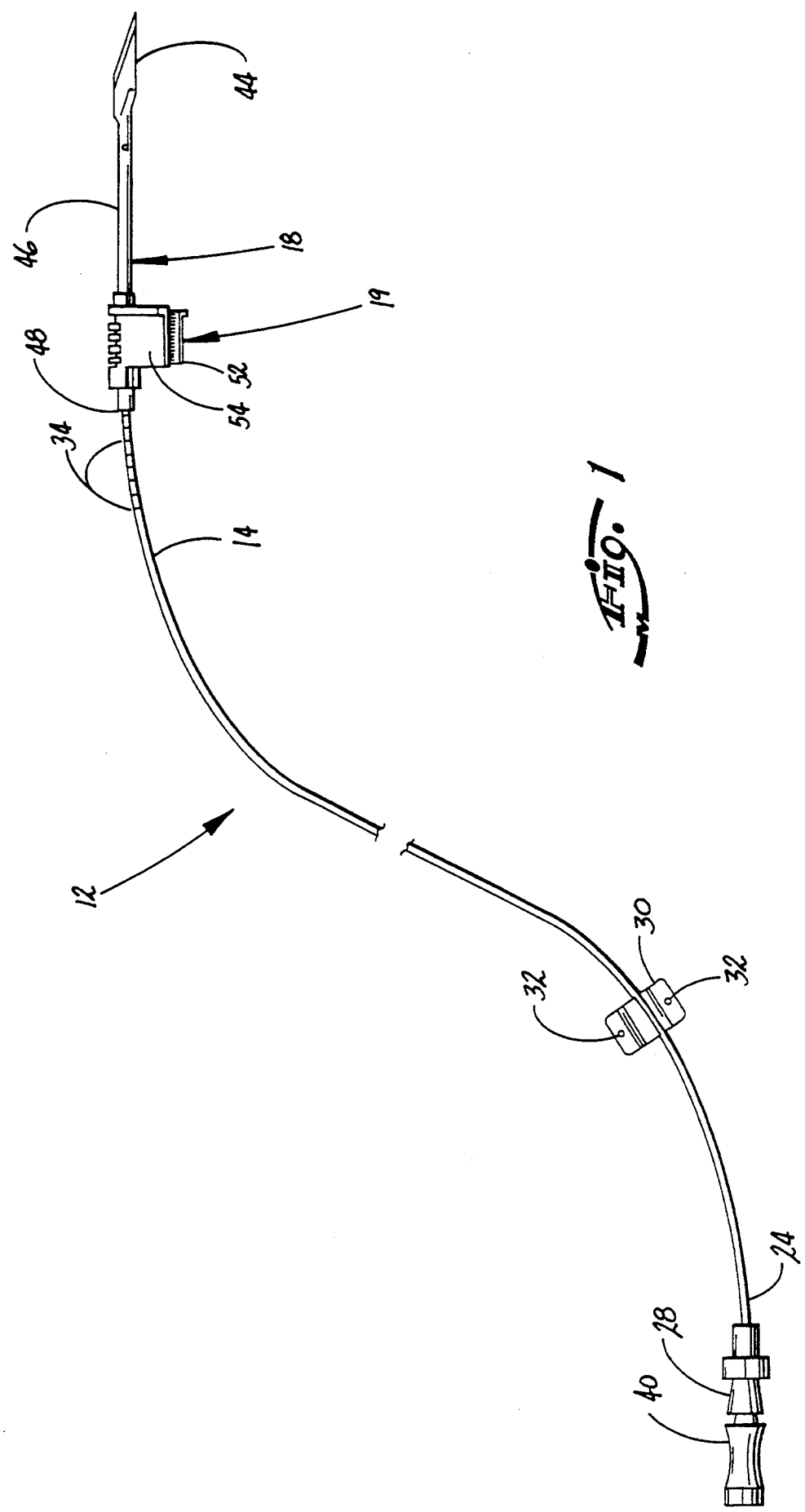
FIG. 1 is an elevational view of a catheter assembly according to the invention.

Referring now to the drawings and to FIGS. 1 to 4 in particular, a catheter assembly 12 comprises a catheter 14, a styler 16 received within the lumen of the catheter 14, and a needle 18 selectively mounted to the catheter 14.

The catheter 14 is preferably formed of a flexible plastic material and has a distal end 22 and a proximal end 24. The distal end 22 is provided with at least one opening, preferably a first opening 20 is formed in the end thereof and at least one side port opening 26 is formed in the side thereof. A female luer connector 28 mounted to the proximal end 24 is used to connect the catheter 14 to a conventional pressure sensing device or aspiration device (not shown) depending upon the particular application for the catheter. The catheter may also carry a series of graduations 34 to indicate the length of the catheter 14 remaining inside the body of the patient.

A suture collar 30 having suture apertures 32 formed therein may be slidably mounted on the catheter 14 to be sutured directly to the patient and secure the catheter 14 in the desired location.

The stylet 16 has an introducer needle 36, a flexible wire member 38 and a handle 40. One end of the wire member 38 is secured to a proximal end of the introducer needle 36 and the other end of the wire is secured to the handle 40. Preferably, the introducer needle 36 is relatively rigid while the wire member 38 is flexible and may be easily manipulated. The stylet 16 is telescopically received in the lumen of the catheter 14 in a manner such that the distal end of the introducer needle 36 is received within the distal end 22 of the catheter 14 when the handle 40 of the stylet 16 abuts the luer connector 28 of the catheter 14. The distal end of the introducer needle 36 comprises a sharpened tip 42.

As seen in FIGS. 3 and 4, the needle 18 comprises a sharpened distal end 44, a hollow body 46 and an open proximal end 48. Preferably, the sharpened distal end 44 is integrally formed with the hollow body 46. The open proximal end 48 and hollow body 46 are adapted to receive the distal end 22 of the catheter 14 together with the introducer needle 36 and wire 38 of the stylet 16. Suitable mounting means are incorporated either in the needle 18, the catheter 14, or the stylet 16 to selectively engage the needle 18 on the catheter 14. In addition, means can be incorporated on the exterior surface of the needle 18 to assist the user in tightly gripping the needle during insertion. Preferably, the exterior surface is toughened by a grit or sand blasting process. The roughened surface preferably extends from the proximal end 48 to the distal end 44. In addition, the exterior surface of the introducer needle 36 is also preferably roughened by a grit or sand blasting process. The entire length of the introducer needle should be roughened.

In the embodiment of the needle 18 shown in FIGS. 1 to 5, the mounting means comprises a slight longitudinal bend or radius imparted to the introducer needle 36. As seen in FIG. 4, the inside diameter of the hollow portion of the needle 18 approximates the outside diameter of the distal end 22 of the catheter 14 with the introducer needle 36 mounted therein. The slight bend in the introducer needle 36 creates a snug, friction fit for the needle 18 on the catheter 14. Alternatively, a slight longitudinal bend or radius can be imparted to the body of the needle 18.

As seen in FIG. 5, one or more detents 50 can be formed in the body of the needle 18. The detents 50 will act as a stop to prevent the tip of the catheter 14 or stylet 16 from being damaged due to over insertion of the catheter 14 and stylet 16 into the needle 18.

The needle 18 is preferably formed from 14 gauge stainless steel hypodermic tubing. The sharpened distal end 44 is formed by flattening the distal end to close the hollow portion. Preferably, the end is flattened in an arbor press to obtain a symmetrically flat end. The flattened end is then shear-cut along an edge diagonal to the longitudinal axis of the body to form a point at the extremity of the distal end. Next, the any remaining burr is removed from the diagonal edge by a whet grinding process.

As seen in FIG. 1, an inserter 19 is selectively mounted on the body of the needle 18. The inserter 19 is substantially U-shaped. The legs of the U-shaped inserter comprise a pair of opposing flanges 52, 54. The bight portion of the U-shaped inserter is generally circular in cross section having a radius slightly less than the radius of the needle 18. The inserter 19 is preferably made of flexible plastic such that the opposing flanges 52, 54 can be squeezed together to cause the inserter 19 to grip the body of the needle 18.

As seen in FIG. 5, the catheter assembly 12 according to the invention can be used to insert the catheter through layers of body tissue 56. Preferably, the catheter assembly 12 according to the invention is inserted outside to inside, i.e. from the skin surface 58 to the wound side 60 of the body tissue 56, although the assembly 12 is also suitable for inside to outside insertion. The needle 18 may be inserted through an incision of appropriate size previously made in the body tissue 56, or an appropriate opening or incision can be created by the sharpened distal end 44 of the needle 18 itself. Regardless of whether the latter method is used, the opening will be of sufficient size to receive the body of the needle 18, and the telescopically mounted catheter 14 and stylet 16. In use, the surgeon mounts the inserter 19 on the body of the needle 18. The surgeon grasps the two opposing flanges 52, 54 and squeezes the flanges to apply a compression force from the inserter 19 to the needle 18. The compression force should be great enough to frictionally engage the inserter 19 on the needle, but not so great as to deform or damage the hollow body of the needle 18. With the proper amount of force applied to the flanges of the inserter 19, the surgeon can then insert the needle 18 through the body tissue 56.

After a portion of the needle 18 has passed through the body tissue 56, the inserter 19 can be removed by spreading the opposing flanges 52, 54 a sufficient distance so that the inserter 19 can be removed therefrom. The needle 18 is grasped from the wound side 60 and pulled through the opening in the body tissue 56. The toughened exterior surface of the needle 18 provides suitable gripping means for the user to grasp the needle 18 and pull the needle 18 and catheter 14 through the opening in the body tissue 56. The needle 18 is then removed and discarded exposing the sterile distal end 22 of the catheter 14 and stylet 16. The distal end 22 of the catheter 14 is positioned at the appropriate location and then the stylet 16 and introducer needle 36 are telescopically removed from the catheter 14. Finally, the luer connector 28 is connected to the appropriate equipment. The graduations 34 mounted on the side of the catheter 14 guide the surgeon in properly locating the catheter 14 within the body cavity.

Figure 6:
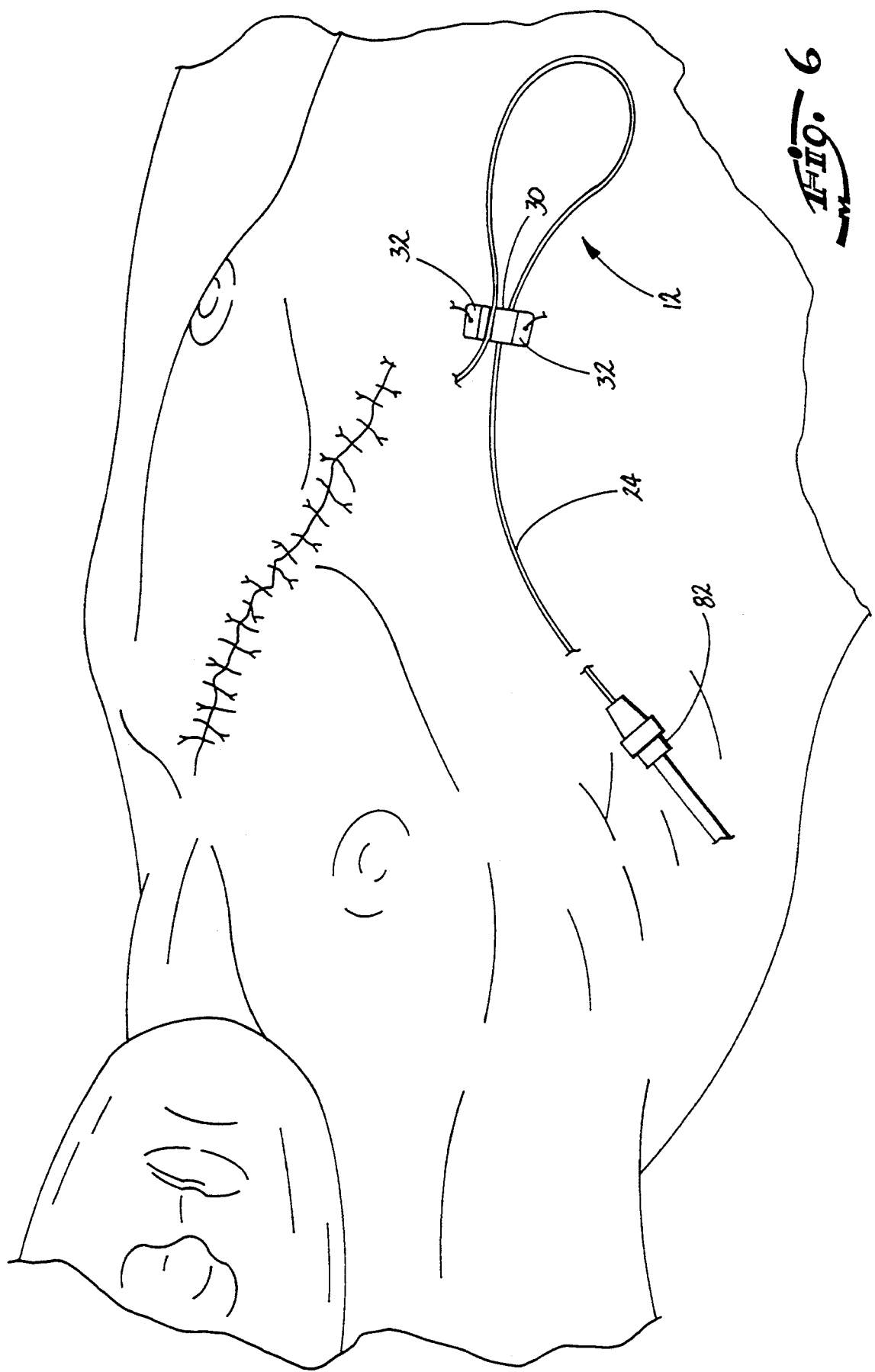
FIG. 6 is a view of a patient having the catheter assembly according to the invention mounted in the chest cavity.

After the catheter 14 has been properly positioned, it may be mounted to the external surface 58 of the patient by suturing the collar 30 to the skin of the patient. As seen in FIG. 6, a portion of the catheter 14 is received in a first groove of the suture collar 30 and a second portion of the catheter 14 is received in a second groove of the suture collar 30. A loop is created in the length of the catheter 14 between the two grooves 30.

Insertion of the catheter 14 employing a catheter assembly 12 according to the invention will provide a significant advantage in reducing the risk of infection of a wound. First, the catheter 14, the needle 18 and the stylet 16 are sterilized. Next, the distal end 22 of the catheter 14 is received within the sterile hollow body 46 of the needle 18. During introduction of the catheter 14 into the patient's body, the needle 18 encounters the patient's skin and is grasped by the user. Any microorganisms residing on the skin surface at the entry side or on the user's hand can contaminate the needle and may adhere to it after it is inserted through the body tissue 56. However, the needle is removed from the catheter 14 and discarded, leaving only the sterile distal end 22 of the catheter 14 inside the body cavity and in contact with the wound, and thus reducing the chance for infection of the wound.

Provision of the needle 18 in the catheter assembly 12 according to the invention also protects the distal end 22 of the catheter from physical damage. For example, if the catheter 14 is to be situated at an intercostal site, the needle 18 will protect the distal end 22 of the catheter 14 from damage due to inadvertent contact with the ribs during insertion.

Referring to FIGS. 7 and 8, a second embodiment 118 of a needle for use in a catheter assembly 12 according to the invention comprises a sharpened distal end 120, a hollow body 122 and an open proximal end 124. As in the first embodiment, the open proximal end 124 and hollow body 122 selectively receive the distal end 22 of the catheter 14 and the distal end 36 of the stylet 16.

The means for selectively mounting the needle 118 to the catheter 14 incorporated in the second embodiment comprises at least one detent 126 which projects into the hollow body 122. As the distal end of the catheter 14 is inserted into the hollow body 122, the side port opening 26 of the catheter engages the detent 126 to selectively mount the catheter 14 within the hollow body 122 of the needle 118.

It is often desirable to insert the catheter assembly externally from the skin surface to the internal or wound side of the patient's tissue. However, as noted above, this has heretofore entailed risk of contamination of the wound, thereby increasing the chances for infection. The catheter assembly according to the invention decreases the chance of infection by shielding the sterile distal end of the catheter from contaminants encountered during insertion of the catheter.

While particular embodiments of the invention have been shown, it will be understood, of course, that the invention is not limited thereto since modifications may be made by those skilled in the art, particularly in light of the foregoing teachings. Reasonable variation and modification are possible within the scope of the foregoing disclosure of the invention without departing from the spirit of the invention.

The embodiments of the invention in which an exclusive property or privilege is claimed are defined as follows:

1. A needle for inserting a catheter through body tissue comprising:
    an elongate body having a hollow portion, a proximal end, and a distal end opposite to the proximal end;
    the distal end comprising a sharpened tip;
    the proximal end of the body being open and in communication with the hollow portion for receiving an end of a catheter in the hollow portion; and
    a longitudinal bend formed in the elongate body for releasably holding within the hollow portion an end of a catheter received therein.

2. A needle according to claim 1 wherein the sharpened tip is integrally formed on the body.

3. A needle according to claim 1 wherein the distal end is flattened to close the hollow portion, and the flattened end is cut along an edge diagonal to the longitudinal axis of the body to form a point at the extremity of the distal end.

4. A needle according to claim 3 wherein the diagonal edge is whet ground to remove burrs from the sharpened tip.

5. A needle according to claim 1 wherein the exterior surface of the needle is roughened to provide a suitable surface for frictionally grasping the needle.

6. A needle for inserting a catheter through body tissue comprising:
    an elongate body having a hollow portion, a proximal end, and a distal end opposite to the proximal end;
    the distal end comprising a sharpened tip;
    the proximal end of the body being open and in communication with the hollow portion for receiving an end of a catheter in the hollow portion; and
    at least one detent protruding inwardly from the interior surface of the hollow portion to limit the received length of an end of a catheter received in the hollow portion.

7. A needle according to claim 6 wherein the detent is situated to cooperate engagingly with corresponding elements of a catheter when the end of the catheter has been received in the hollow portion to a predetermined length thereof.

8. A needle according to claim 6 and further comprising a pair of diametrically opposed detents protruding inwardly from the interior surface of the hollow portion to limit the received length of an end of a catheter received in the hollow portion.

9. A needle according to claim 8 wherein the detents comprise indentations of the exterior surface of the hollow portion.

10. A needle according to claim 6 wherein the sharpened tip is integrally formed on the body.

11. A needle according to claim 6 wherein the distal end is flattened to close the hollow portion, and the flattened end is cut along an edge diagonal to the longitudinal axis of the body to form a point at the extremity of the distal end.

12. A needle according to claim 6 wherein the exterior surface of the needle is roughened to provide a suitable surface for frictionally grasping the needle.

13. A catheter assembly comprising:
a catheter having a proximal end, a distal end and a lumen extending therethrough, the proximal end being opposite the distal end;
a needle having an elongate body at least a portion of which is hollow, a distal end and a proximal end, the distal end comprising a sharpened tip, the proximal end being opposite the distal end and the proximal end of the hollow body being open and in communication with the hollow portion for receiving the distal end of the catheter; and
at least one detent protruding inwardly from the interior surface of the hollow portion to limit the received length of the distal end of the catheter received in the hollow portion of the needle and to releasably hold the catheter within the hollow portion of the needle.

14. A catheter assembly according to claim 13 wherein the detent is situated to cooperate engagingly with corresponding elements of the catheter when the distal end of the catheter has been received in the hollow portion to a predetermined length thereof.

15. A catheter assembly according to claim 13 and further comprising a pair of diametrically opposed detents protruding inwardly from the interior surface of the hollow portion to limit the received length of the distal end of the catheter received in the hollow portion.

16. A catheter assembly according to claim 15 wherein the detents comprise indentations of the exterior surface of the hollow portion.

17. A catheter assembly according to claim 13 and further comprising a stylet telescopically received within the lumen of the catheter, the stylet having a distal and a proximal end, the distal end being opposite the proximal end.

18. A catheter assembly according to claim 13 wherein the sharpened tip is integrally formed on the body.

19. A catheter assembly according to claim 13 wherein the distal end is flattened to close the hollow portion, and the flattened end is cut along an edge diagonal to the longitudinal axis of the body to form a point at the extremity of the distal end.

20. A catheter assembly according to claim 19 wherein the diagonal edge is whet ground to remove burrs from the sharpened tip.

21. A catheter assembly according to claim 13 further comprising a plurality of graduations mounted on the distal end of the catheter body to indicate the depth of the catheter received in a body cavity.

22. A catheter assembly according to claim 13 further comprising an inserter selectively received on the body of the needle, the inserter functioning as a handle for gripping the needle.

23. A catheter assembly comprising:
a catheter having a proximal end, a distal end and a lumen extending therethrough, the proximal end being opposite the distal end;
a needle having an elongate body at least a portion of which is hollow, a distal end and a proximal end, the distal end comprising a sharpened tip, the proximal end being opposite the distal end and the proximal end of the hollow body being open and in communication with the hollow portion for receiving the proximal end of the catheter; and
a stylet telescopically received within the lumen of the catheter, the stylet having a distal and a proximal end, the proximal end being opposite the distal end, the distal end of the stylet comprising a rigid introducer needle having a slight longitudinal bend imparted to the introducer needle such that the catheter is frictionally retained within the hollow portion of the needle.

24. A catheter assembly according to claim 23 wherein the exterior surface of the introducer needle is roughened, the roughened surface extending along the entire length of the introducer needle.

25. A catheter assembly according to claim 23 wherein the sharpened tip is integrally formed on the body.

26. A catheter assembly according to claim 23 wherein the distal end is flattened to close the hollow portion, and the flattened end is cut along an edge diagonal to the longitudinal axis of the body to form a point at the extremity of the distal end.

27. A catheter assembly according to claim 23 further comprising a plurality of graduations mounted on the distal end of the catheter body to indicate the depth of the catheter received in a body cavity.

28. A catheter assembly according to claim 23 further comprising an inserter selectively received on the body of the needle, the inserter functioning as a handle for gripping the needle.

29. A catheter assembly comprising:
a catheter having a proximal end, a distal end and a lumen extending therethrough, the proximal end being opposite the distal end;
a needle having an elongate body at least a portion of which is hollow, a distal end and a proximal end, the proximal end being opposite the distal end, the distal end comprising a sharpened tip, the proximal end of the hollow body being open and in communication with the hollow portion for receiving the distal end of the catheter; and
a stylet telescopically received within the lumen of the catheter, the stylet having a proximal end and a distal end, the distal end of the stylet comprising a rigid introducer needle having a slight longitudinal bend imparted thereto;
wherein the introducer needle is telescopically received in the proximal end of the catheter and the needle is selectively retained on the distal end of the catheter because of the slight longitudinal bend of the introducer needle.

* * * * *